United States Patent [19]
Haynes et al.

[11] Patent Number: 5,941,862
[45] Date of Patent: Aug. 24, 1999

[54] ABSORBENT STRUCTURE HAVING ZONES SURROUNDED BY A CONTINUOUS REGION OF HYDROGEL FORMING ABSORBENT POLYMER

[75] Inventors: Nancy Ann Haynes; Gerald Alfred Young, both of Cincinnati, Ohio

[73] Assignee: The Procter & Gamble, Cincinnati, Ohio

[21] Appl. No.: 08/910,478

[22] Filed: Jul. 25, 1997

Related U.S. Application Data

[63] Continuation of application No. 08/585,278, Jan. 11, 1996, abandoned.

[51] Int. Cl.⁶ .................................................. A61F 13/15
[52] U.S. Cl. .......................... 604/368; 604/372; 604/378
[58] Field of Search ..................................... 604/358, 367, 604/368, 372, 378, 385.1

[56] References Cited

U.S. PATENT DOCUMENTS

| | | |
|---|---|---|
| Re. 32,649 | 4/1988 | Brandt et al. . |
| 3,669,103 | 6/1972 | Harper et al. . |
| 3,670,731 | 6/1972 | Harmon . |
| 3,770,731 | 11/1973 | Jaeger . |
| 3,929,135 | 12/1975 | Thompson . |
| 3,959,569 | 5/1976 | Burkholder, Jr. . |
| 4,055,180 | 10/1977 | Karami . |
| 4,260,443 | 4/1981 | Lindsay et al. . |
| 4,324,246 | 4/1982 | Mullane et al. . |
| 4,327,728 | 5/1982 | Elias . |
| 4,342,314 | 8/1982 | Radel et al. . |
| 4,360,021 | 11/1982 | Stima . |
| 4,381,783 | 5/1983 | Elias . |
| 4,463,045 | 7/1984 | Ahr et al. . |
| 4,560,372 | 12/1985 | Pieniak ..................................... 604/368 |
| 4,600,458 | 7/1986 | Kramer et al. . |
| 4,609,518 | 9/1986 | Curro et al. . |
| 4,625,001 | 11/1986 | Tsubakimoto et al. . |
| 4,629,643 | 12/1986 | Curro et al. . |
| 4,654,039 | 3/1987 | Brandt et al. . |
| 4,666,983 | 5/1987 | Tsubakimoto . |
| 4,670,011 | 6/1987 | Mesek . |
| 4,673,402 | 6/1987 | Weisman et al. . |
| 4,834,735 | 5/1989 | Alemany et al. . |
| 4,851,069 | 7/1989 | Packard et al. . |
| 4,935,022 | 6/1990 | Lash et al. . |
| 4,950,254 | 8/1990 | Andersen et al. . |
| 4,960,477 | 10/1990 | Mesek . |
| 4,994,053 | 2/1991 | Lang . |
| 5,006,394 | 4/1991 | Baird . |
| 5,009,650 | 4/1991 | Bernardin . |
| 5,061,259 | 10/1991 | Goldman et al. . |
| 5,102,597 | 4/1992 | Roe et al. . |
| 5,128,082 | 7/1992 | Makoui . |
| 5,149,335 | 9/1992 | Kellenberger et al. . |
| 5,324,561 | 6/1994 | Rezai et al. . |
| 5,411,497 | 5/1995 | Tanzer et al. ............................ 604/368 |

FOREIGN PATENT DOCUMENTS

| | | |
|---|---|---|
| 0 160 572 | 11/1985 | European Pat. Off. . |
| 0 443 627 A2 | 8/1991 | European Pat. Off. . |
| 0 624 618 | 11/1994 | European Pat. Off. . |
| 0 700 672 | 3/1996 | European Pat. Off. . |
| WO 91/03999 | 4/1991 | WIPO . |
| 0 615 736 A1 | 9/1994 | WIPO . |
| WO 95/10995 | 4/1995 | WIPO . |
| WO 95/17870 | 7/1995 | WIPO . |

*Primary Examiner*—Mark O. Polutta
*Attorney, Agent, or Firm*—Kevin D. Hogg; Steven W. Miller; Jacobus C. Rasser

[57] ABSTRACT

Disclosed are absorbent structures comprising a first layer, a second layer juxtaposed in facing relation with said first layer, wherein at least one of the layers is fluid pervious. These structures also have a continuous region between said first and second layers comprising hydrogel-forming polymer that is substantially uniformly distributed throughout the region. The continuous region at least partially surrounds multiple, spaced apart zones between said layers, which zones are substantially devoid of hydrogel-forming absorbent polymer. The first and second layers are bonded together such that said hydrogel-forming absorbent polymer is substantially immobilized when in dry state, preferably at sites within a plurality of the zones. Preferably, the hydrogel-forming polymer has relatively high gel permeability such that it forms a gel-continuous fluid transportation layer.

20 Claims, 1 Drawing Sheet

ABSORBENT STRUCTURE HAVING ZONES SURROUNDED BY A CONTINUOUS REGION OF HYDROGEL FORMING ABSORBENT POLYMER

This is a Continuation of U.S. application Ser. No. 08/585,278, filed Jan. 11, 1996, now abandoned.

BACKGROUND OF THE INVENTION

The development of highly absorbent members for use as disposable diapers, adult incontinence pads and briefs, and catamenial products such as sanitary napkins, are the subject of substantial commercial interest. A highly desired characteristic for such products is thinness. For example, thinner diapers are less bulky to wear, fit better under clothing, and are less noticeable. They are also more compact in the package, making the diapers easier for the consumer to carry and store. Compactness in packaging also results in reduced distribution costs for the manufacturer and distributor, including less shelf space required in the store per diaper unit.

The ability to provide thinner absorbent articles such as diapers has been contingent on the ability to develop relatively thin absorbent cores or structures that can acquire and store large quantities of discharged body fluids, in particular urine. In this regard, the use of certain absorbent polymers often referred to as "hydrogels," "superabsorbents" or "hydrocolloid" material has been particularly important. See, for example, U.S. Pat. No. 3,699,103 (Harper et al) issued Jun. 13, 1972, and U.S. Pat. No. 3,670,731 (Harmon) issued Jun. 20, 1972, that disclose the use of such absorbent polymers (hereafter "hydrogel-forming absorbent polymers") in absorbent articles. Indeed, the development of thinner diapers has been the direct consequence of thinner absorbent cores that take advantage of the ability of these hydrogel-forming absorbent polymers to absorb large quantities of discharged body fluids, typically when used in combination with a fibrous matrix. See, for example, U.S. Pat. No. 4,673,402 (Weisman et al) issued Jun. 16, 1987, and U.S. Pat. No. 4,935,022 (Lash et al) issued Jun. 19, 1990, that disclose dual-layer core structures comprising a fibrous matrix and hydrogel-forming absorbent polymers useful in fashioning thin, compact, nonbulky diapers.

Prior to the use of these hydrogel-forming absorbent polymers, it was general practice to form absorbent structures, such as those suitable for use in infant diapers, entirely from wood pulp fluff. Given the relatively low amount of fluid absorbed by wood pulp fluff on a gram of fluid absorbed per gram of wood pulp fluff, it was necessary to employ relatively large quantities of wood pulp fluff, thus necessitating the use of relatively bulky, thick absorbent structures. The introduction of these hydrogel-forming absorbent polymers into such structures has allowed the use of less wood pulp fluff. These hydrogel-forming absorbent polymers are superior to fluff in their ability to absorb large volumes of aqueous body fluids, such as urine (i.e., at least about 15 g/g), thus making smaller, thinner absorbent structures feasible.

Prior absorbent structures have generally comprised relatively low amounts (e.g., less than about 50% by weight) of these hydrogel-forming absorbent polymers. See, for example, U.S. Pat. No. 4,834,735 (Alemany et al) issued May 30, 1989 (preferably from about 9 to about 50% hydrogel-forming absorbent polymer in the fibrous matrix). There are several reasons for this. The hydrogel-forming absorbent polymers employed in prior absorbent structures have generally not had an absorption rate that would allow them to quickly absorb body fluids, especially in "gush" situations. This has necessitated the inclusion of fibers, typically wood pulp fibers, to serve as temporary reservoirs to hold the discharged fluids until absorbed by the hydrogel-forming absorbent polymer.

More importantly, many of the known hydrogel-forming absorbent polymers exhibited gel blocking, especially when included in the absorbent structure at higher levels. "Gel blocking" occurs when particles of the hydrogel-forming absorbent polymer are wetted and the particles swell so as to inhibit fluid transmission to other regions of the absorbent structure. Wetting of these other regions of the absorbent structure therefore takes place via a very slow diffusion process. In practical terms, this means acquisition of fluids by the absorbent structure is much slower than the rate at which fluids are discharged, especially in gush situations. Leakage from the absorbent article can take place well before the particles of hydrogel-forming absorbent polymer in the absorbent structure are fully saturated or before the fluid can diffuse or wick past the "blocking" particles into the rest of the absorbent structure. Gel blocking can be a particularly acute problem if the particles of hydrogel-forming absorbent polymer do not have adequate gel strength and deform or spread under stress once the particles swell with absorbed fluid. See U.S. Pat. No. 4,834,735 (Alemany et al) issued May 30, 1989.

This gel blocking phenomena has typically necessitated the use of a fibrous matrix in which are dispersed the particles of hydrogel-forming absorbent polymer. This fibrous matrix keeps the particles of hydrogel-forming absorbent polymer separated from one another. This fibrous matrix also provides a capillary structure that allows fluid to reach the hydrogel-forming absorbent polymer located in regions remote from the initial fluid discharge point. See U.S. Pat. No. 4,834,735 (Alemany et al) issued May 30, 1989. However, dispersing the hydrogel-forming absorbent polymer in a fibrous matrix at relatively low concentrations in order to minimize or avoid gel blocking can lower the overall fluid storage capacity of thinner absorbent structures. Using lower concentrations of these hydrogel-forming absorbent polymers limits somewhat the real advantage of these materials, namely their ability to absorb and retain large quantities of body fluids per given volume. In addition, the particles of hydrogel-forming absorbent polymer may not be immobilized in this fibrous matrix and may be free to migrate during processing and/or use. This migration of particles, especially as the hydrogel-forming absorbent polymer swells, can contribute to gel blocking.

One method for increasing the relative concentration of hydrogel-forming absorbent polymer is to form a layer thereof between two other fibrous layers, e.g., a laminate structure. See, for example, U.S. Pat. No. 4,600,458 (Kramer et al) issued Jul. 15, 1986, and U.S. Pat. No. 5,009,650 (Bernardin) issued Apr. 23, 1991. The fibrous layers of prior laminate structures have often been held together by hydrogen bonding as a result of spraying the fibrous layers with water, typically followed by compaction. See U.S. Pat. No. 4,260,443 (Lindsay et al) issued Apr. 7, 1981, U.S. Pat. No. 4,360,021 (Stima) issued Nov. 23, 1982, and U.S. Pat. No. 4,851,069 (Packard et al) issued Jul. 25, 1989. These prior laminate structures have also been held together by adhesive bonding between the fibrous layers or between the fibrous layers and the hydrogel-forming absorbent polymer. See U.S. Pat. No. 4,994,053 (Lang) issued Feb. 19, 1991 (pattern of adhesive or heat fusible films), and U.S. Pat. No. 5,128,082 (Makoui) issued Jul. 7, 1992 (latex coating). By encapsulating the particles of hydrogel-forming absorbent polymer between these fibrous layers (especially those held together by hydrogen bonding or adhesive bonding), the overall particle mobility within the absorbent structure is also greatly reduced.

As the hydrogel-forming absorbent polymer is contacted with fluid, it can swell to a significant volume. This can cause problems with laminate structures, especially those containing high concentrations of hydrogel-forming absorbent polymer. The fibrous layers of the laminate can restrict the ability of the hydrogel-forming absorbent polymer to expand as it is contacted with additional fluid, thus limiting the overall fluid capacity of the structure. Laminates held together by hydrogen bonding can have insufficient integrity, especially as the structure becomes saturated with fluid. Adhesive bonding, especially when the adhesive is hydrophobic and/or coats the hydrogel-forming absorbent polymer, can also decrease the total fluid capacity of the structure.

Some of these prior laminate structures have involved the formation of discrete, spaced pockets of hydrogel-forming absorbent polymer particles. See U.S. Pat. No. 4,360,021 (Stima) issued Nov. 23, 1982 (backsheet 13 and cover sheet 15 made of tissue wadding that is selectively compressed to form pockets of hydrogel-forming absorbent polymer particles 24), U.S. Pat. No. 4,994,053 (Lang) issued Feb. 19, 1991 (pattern of adhesive 60, as well as heat fusible films 68 and 70, to form pockets of hydrogel-forming absorbent polymer particles 56/58), U.S. Pat. No. 4,055,180 (Karami) issued Oct. 25, 1977 (retaining sheet 56 that is preferably a thermoplastic film fused to wadding sheet 40 by heat to form pockets of hydrogel-forming absorbent polymer particles 62), and U.S. Pat. No. 5,149,335 (Kellenberger et al) issued Sep. 22, 1992 (outer cover 22 bonded to body-side liner 24 along bond lines 28 to form compartments 30 of hydrogel-forming absorbent polymer particles 32).

Laminate structures having these discrete pockets of particles form an essentially "discontinuous" layer or pattern of hydrogel-forming absorbent polymer. Since the hydrogel-forming absorbent polymer is a discontinuous layer, it may be more difficult for the fluid to reach each of the discrete pockets. Indeed, in some of these "discontinuous" laminate structures, the discrete pockets of hydrogel-forming absorbent polymer are not in direct fluid communication. Moreover, these discrete pockets of hydrogel-forming absorbent polymer can form protuberances that are undesirable aesthetically and can make the absorbent article uncomfortable for the wearer.

Laminate structures based on discrete pockets of hydrogel-forming absorbent polymer particles also do not take much advantage of any inherent gel permeability of the hydrogel formed when these absorbent polymers swell in the presence of body fluids. It is believed that when a hydrogel-forming absorbent polymer is present at high concentrations in an absorbent structure and then swells to form a hydrogel under usage pressures, the boundaries of the hydrogel come into contact, and interstitial voids in this high-concentration region become generally bounded by hydrogel. When this occurs, it is believed the gel permeability properties of this region are generally reflective of the permeability properties of a hydrogel zone or layer formed from the hydrogel-forming absorbent polymer alone. This allows this hydrogel layer to transport and distribute fluids at rates that more closely approach those of a fibrous web. Hydrogel layers that are formed as discrete, discontinuous pockets will only marginally utilize, if at all, these inherent gel permeability properties.

Accordingly, it would be desirable to provide absorbent structures that: (1) have high concentrations of hydrogel-forming absorbent polymer; (2) can immobilize the hydrogel-forming absorbent polymer without restricting the ability of it to expand as it is contacted with additional fluid; and (3) takes advantage of the inherent gel permeability properties of the resulting hydrogel that forms.

SUMMARY OF THE INVENTION

The present invention provides an absorbent structure comprising a first layer, a second layer juxtaposed in facing relation with said first layer, wherein at least one of the layers is fluid pervious. These structures also have a continuous region between said first and second layers comprising hydrogel-forming polymer that is substantially uniformly distributed throughout the region. The continuous region surrounds multiple, spaced apart zones between said layers, which zones are substantially devoid of hydrogel-forming absorbent polymer. The first and second layers are bonded together such that said hydrogel-forming absorbent polymer is substantially immobilized when in dry state, preferably at sites within a plurality of the zones. Preferably, the hydrogel-forming polymer has relatively high gel permeability such that it forms a gel-continuous fluid transportation layer.

Unlike prior laminated structures, the absorbent structures of the present invention provide space (i.e., zones) that allow expansion of the hydrogel-forming absorbent polymer as it swells. This allows fuller utilization of the total fluid capacity of the hydrogel-forming absorbent polymer. The zones substantially devoid of hydrogel-forming absorbent polymer also permit selective bonding of the layers to provide wet and dry integrity, without adversely affecting ability of the absorbent structure to transport and distribute fluid.

Also unlike prior laminate structures having discrete pockets of hydrogel-forming absorbent polymer, the absorbent structures of the present invention have a continuous region of hydrogel-forming absorbent polymer. This allows the resulting continuous hydrogel layer formed to take advantage of any inherent gel permeability properties of the hydrogel-forming absorbent polymer. Also, the zones substantially devoid of hydrogel-forming absorbent polymer are essentially in fluid communication with this continuous region. Accordingly, these zones provide an effective medium for distributing fluid to more of the hydrogel-forming absorbent polymer in this continuous region to more effectively utilize the total fluid capacity of the absorbent structure.

The absorbent structures of the present invention are particularly useful as absorbent cores for a variety of disposable products which are capable of absorbing significant quantities of body fluids, such as urine and water in body fluids. These products include disposable diapers, adult incontinence briefs, adult incontinence pads, sanitary napkins, tampons, training pants and the like.

DETAILED DESCRIPTION OF THE INVENTION

A. Definitions

Figure 1:
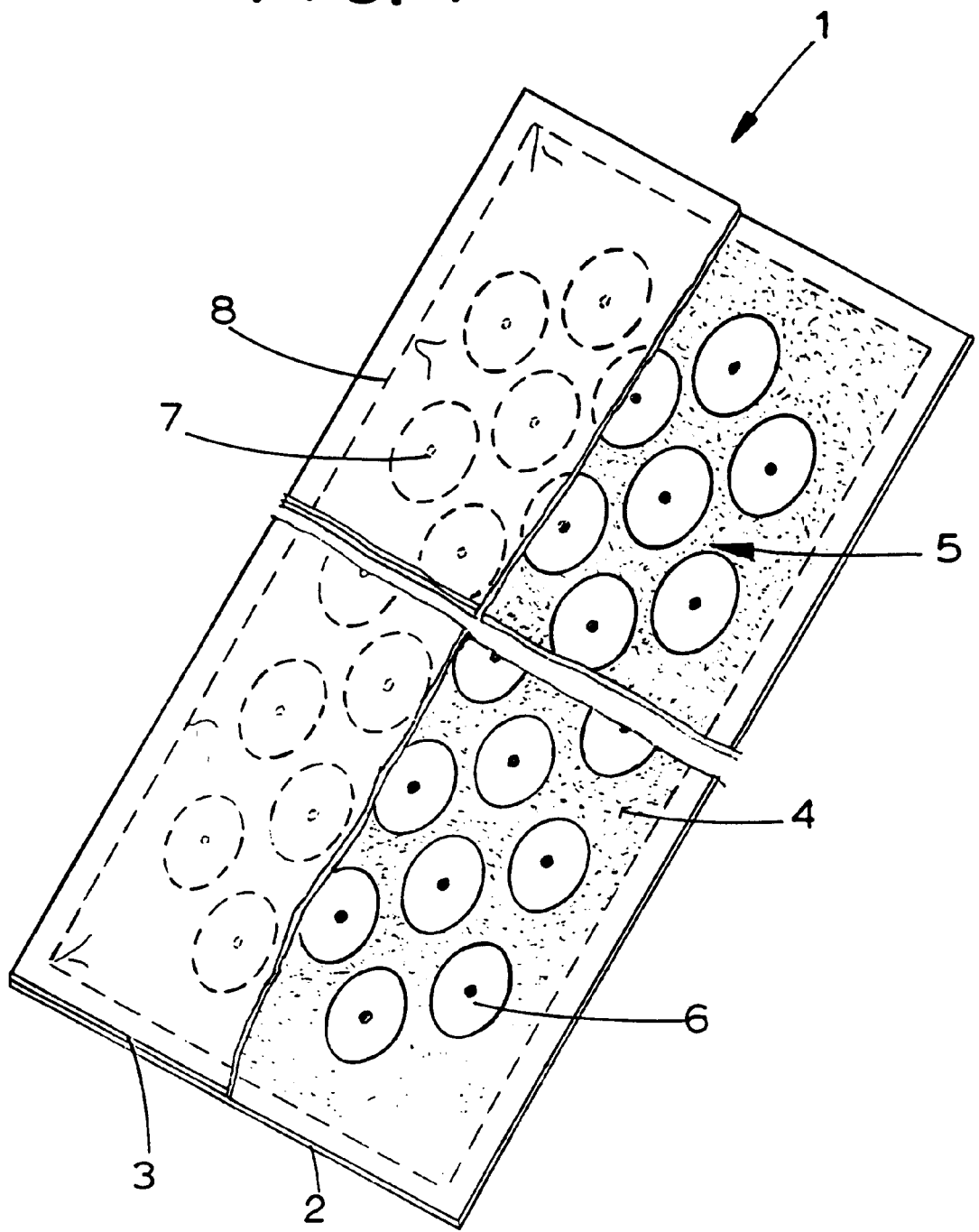
FIG. 1 represents a perspective view of one embodiment of an absorbent structure of the present invention.

In the context of the present invention, the term "fluid" means "liquid."

As used herein, the term "body fluids" includes urine, menses, vaginal discharges and watery portions of bodily wastes.

As used herein, the term "layer" refers to a member whose primary dimension is X-Y, i.e., along its length and width. It should be understood that the term layer is not necessarily limited to single layers of material. Thus the term layer can comprise combinations of several sheets or webs of the requisite type of materials. Accordingly, the term "layer" includes the terms "layers" and "layered."

As used herein, the terms "stretch" and "percent stretch" refer to the degree to which an extensible layer adjacent the hydrogel-forming polymer can be elongated in at least one direction to a strain corresponding to its tensile strength. Percent stretch is determined using the following formula:

$$\left\{ \frac{\begin{array}{c}\text{(Length of Layer Stretched to Strain}\\ \text{Corresponding to its Tensile Strength)} -\\ \text{(Length of Layer Unstretched)}\end{array}}{\text{(Length of Layer Unstretched)}} \right\} \times 100$$

The degree of stretch of a given layer includes both the natural strain of the material utilized, and elongation/stretch after folding, crimping, etc. Thus, the length of the layer unstretched (i.e., "unextended") is measured after the layer is folded, crimped, etc.

As used herein, the term "comprising" means various components, members, steps and the like can be conjointly employed according to the present invention. Accordingly, the term "comprising" encompasses the more restrictive terms "consisting essentially of" and "consisting of," these latter, more restrictive terms having their standard meaning as understood in the art.

All percentages, ratios and proportions used herein are by weight unless otherwise specified.

B. Layers

The absorbent structures of the invention comprise a first layer, as well as a second layer juxtaposed in facing relation with the first layer. These layers can comprise fibrous materials which form a fibrous web or fibrous matrix. Fibers useful in the present invention include those that are naturally occurring fibers (modified or unmodified), as well as synthetically made fibers. Examples of suitable unmodified or modified naturally occurring fibers include cotton, Esparto grass, bagasse, kemp, flax, silk, wool, wood pulp, chemically modified wood pulp, jute, rayon, ethyl cellulose, and cellulose acetate. Suitable synthetic fibers can be made from polyvinyl chloride, polyvinyl fluoride, polytetrafluoroethylene, polyvinylidene chloride, polyacrylics such as ORLON®, polyvinyl acetate, polyethylvinyl acetate, non-soluble or soluble polyvinyl alcohol, polyolefins such as polyethylene (e.g., PULPEX®) and polypropylene, polyamides such as nylon, polyesters such as DACRON® or KODE®, polyurethanes, polystyrenes, and the like. The fibers used can comprise solely naturally occurring fibers, solely synthetic fibers, or any compatible combination of naturally occurring and synthetic fibers.

The fibers used in these layers can be hydrophilic, hydrophilized hydrophobic, or can be a combination of both hydrophilic and hydrophobic fibers. As used herein, the term "hydrophilic" describes fibers, or surfaces of fibers, that are wettable by aqueous fluids (e.g., aqueous body fluids) deposited on these fibers. Hydrophilicity and wettability of individual fibers is typically defined in terms of contact angle and the surface tension of the fluids and solids involved. This is discussed in detail in the American Chemical Society publication entitled *Contact Angle, Wettability and Adhesion*, edited by Robert F. Gould (Copyright 1964).

A fiber, or surface of a fiber, is said to be wetted by a fluid (i.e., hydrophilic) when either the contact angle between the fluid and the fiber, or its surface, is less than 90°, or when the fluid tends to spread spontaneously across the surface of the fiber, both conditions normally co-existing. Conversely, a fiber or surface is considered to be hydrophobic if the contact angle is greater than 90° and the fluid does not spread spontaneously across the surface of the fiber.

The particular selection of hydrophilic or hydrophobic fibers will depend upon the fluid handling properties and other characteristics desired for the resulting layer. Generally the use of hydrophilic fibers in these layers is preferred. This is especially true for layers that are desired to efficiently acquire discharged body fluids, and then quickly transfer and distribute the acquired fluid to other, remote regions of the absorbent structure.

Suitable hydrophilic fibers for use in the present invention include cellulosic fibers, modified cellulosic fibers, rayon, polyester fibers such as polyethylene terephthalate (e.g., DACRON®), hydrophilic nylon (HYDROFIL®), and the like. Suitable hydrophilic fibers can also be obtained by hydrophilizing hydrophobic fibers, such as surfactant-treated or silica-treated thermoplastic fibers derived from, for example, polyolefins such as polyethylene or polypropylene, polyacrylics, polyamides, polystyrenes, polyurethanes and the like. For reasons of availability and cost, cellulosic fibers, in particular wood pulp fibers, are preferred for use in the present invention.

Suitable wood pulp fibers can be obtained from well-known chemical processes such as the Kraft and sulfite processes. It is especially preferred to derive these wood pulp fibers from southern soft woods due to their premium absorbency characteristics. These wood pulp fibers can also be obtained from mechanical processes, such as ground wood, refiner mechanical, thermomechanical, chemimechanical, and chemi-thermomechanical pulp processes. Recycled or secondary wood pulp fibers, as well as bleached and unbleached wood pulp fibers, can be used.

It is further preferred that the layers of the present invention comprise thermoplastic material in addition to the fibers. Upon melting, at least a portion of this thermoplastic material migrates to the intersections of the fibers, typically due to interfiber capillary gradients. These intersections become bond sites for the thermoplastic material. When cooled, the thermoplastic materials at these intersections solidify to form the bond sites that hold the matrix or web of fibers together in each of the respective layers. Amongst its various effects, bonding at these fiber intersections increases the overall compressive modulus and strength of the resulting layer.

Thermoplastic materials useful in the present invention can be in any of a variety of forms including particulates, fibers, or combinations of particulates and fibers. Thermoplastic fibers are a particularly preferred form because of their ability to form numerous interfiber bond sites. Suitable thermoplastic materials can be made from any thermoplastic polymer that can be melted at temperatures that will not extensively damage the fibers that comprise the primary web or matrix of each layer. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in absorbent articles, are likely to be stored. The melting point of the thermoplastic material is typically no lower than about 50° C.

The thermoplastic materials, and in particular the thermoplastic fibers, can be made from a variety of thermoplastic polymers, including polyolefins such as polyethylene (e.g., PULPEX®) and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the foregoing such as vinyl chloride/vinyl acetate, and the like. One suitable thermoplastic binder fiber is PLEXAFIL® polyethylene microfibers (made by DuPont) that are also available as an about 20% blend with 80% cellulosic fibers sold under the tradename KITTY-HAWK® (made by Weyerhaeuser Co.) Depending upon the desired characteristics for the resulting layer, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij® 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g/cm$^2$ of thermoplastic fiber.

Suitable thermoplastic fibers can be made from a single polymer (monocomponent fibers), or can be made from more than one polymer (e.g., bicomponent fibers). As used herein, "bicomponent fibers" refers to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp.

It is preferred that at least one of the layers of the present invention be extensible. It is believed extensibility allows the hydrogel-forming absorbent polymer, distributed between the layers, additional, relatively unconstrained room to swell upon imbibing fluid. This is desirable, for example, because particles which are unduly constrained from swelling cannot reach their full absorbency potential. In general, layers having an unextended basis weight in the range of from about 0.001 g/cm$^2$ to about 0.30 g/cm$^2$, preferably from about 0.002 g/cm$^2$ to about 0.10 g/cm$^2$, more preferably from about 0.002 g/cm$^2$ to about 0.05 g/cm$^2$, most preferably from about 0.002 to about 0.03 g/cm$^2$; a density range under a confining pressure of 0.2 psi (1.4 kPa) of from about 0.02 g/cc to about 0.40 g/cc; and a percent stretch of at least about 5%, preferably from about 5 to about 50%, are suitable for use in the present invention. (As used herein, the terms unstretched and unextended are synonymous.) A particularly preferred layer is a thermobonded airlaid blend of 75% Flint River wood pulp fluff and 25% DANAKLON® ES-C 1.7X6 bicomponent fibers, having an uncreped basis weight of 0.0034 g/cm$^2$ and density of 0.144 g/cc, which is creped to have a stretch of 35% and post-crepe basis weight of 0.0045 g/cm$^2$. At least one of the layers of the present invention must be fluid pervious to allow fluids to reach the hydrogel-forming polymer distributed between the layers. Depending on the application, it may be desired that both layers be fluid pervious, or alternatively, that one of the layers (typically, the layer furthermost away from the wearer of the absorbent article) be fluid impervious. Fluid impervious layers can be manufactured from a thin plastic film, although other flexible fluid impervious materials can also be used. A suitable fluid impervious material is a polyethylene film having a thickness of from about 0.01 millimeters to about 0.05 centimeters.

C. Continuous Region of Hydrogel-Forming Absorbent Polymer

The absorbent structures of the present invention further comprise hydrogel-forming absorbent polymer between the first and second layers. In particular, the hydrogel-forming absorbent polymer is substantially uniformly distributed throughout a continuous region between the layers. As used herein, "continuous region" means a region where a path, although not necessarily a straight line path, exists between any point in the region and all other points in the region without having to pass through any zone (hereinafter described) that is substantially devoid of hydrogel-forming absorbent polymer. This continuous region can be in the form of an absorbent macrostructure made from particles of these hydrogel-forming absorbent polymers such as disclosed in, for example, U.S. Pat. No. 5,102,597 (Roe et al) issued Apr. 7, 1992, and U.S. Pat. No. 5,324,561 (Rezai et al) issued Jun. 23, 1994, both of which are incorporated by reference. Typically, this continuous region comprises discrete particles of hydrogel-forming polymer between the first and second layers. It is believed that a substantially uniform distribution of the hydrogel-forming absorbent polymer particles in a continuous region provides an uninterrupted path for fluid to travel from particle to particle throughout the entire region, particularly where the hydrogel-forming absorbent polymer is present at high concentrations and has a relatively high gel permeability when swollen.

The preferred hydrogel-forming absorbent polymer concentration/weight per unit area (referred to herein as "basis weight") between the layers is at least about 0.001 g/cm$^2$, preferably at least about 0.002 g/cm$^2$, more preferably at least about 0.005 g/cm², and most preferably at least about 0.010 g/cm². Typically these basis weight values are in the range of from about 0.001 g/cm² to about 0.100 g/cm², more typically from about 0.005 g/cm² to about 0.080 g/cm², and most typically from about 0.01 g/cm² to about 0.06 g/cm². In measuring basis weight of the hydrogel forming polymer, the area measurement is the smallest area that encompasses the entire patterned hydrogel region and includes the area of any substantially hydrogel-free zones (hereinafter described) encompassed by this region. To enhance dry stability and inhibit dry hydrogel-forming absorbent polymer particles from shifting between the layers, the particles may be slightly moistened (for example, misted) with water just prior to or after the particles are distributed to cause the formation of hydrogen bonds between the particles and layers. Because of their nature, such hydrogen bonds will typically release when the particles are rewetted with body fluids during use.

The hydrogel-forming polymers used in the absorbent structures of the present invention are those materials which, upon contact with fluids such as water or body fluids, imbibe such fluids and thereby form hydrogels. In this manner, fluid discharged into the absorbent structure can be acquired and held by the hydrogel-forming absorbent polymers. The hydrogel-forming polymers which are employed will generally comprise particles of a substantially water-insoluble, slightly cross-linked, partially neutralized, hydrogel-forming polymer material. Such polymer materials are described, for example, in U.S. Pat. No. 5,061,259 (Goldman et. al) issued Oct. 29, 1991, U.S. Pat. No. 4,654, 039 (Brandt et al) issued Mar. 31, 1987 (reissued Apr. 19, 1988 as Re. 32,649), U.S. Pat. No. 4,666,983 (Tsubakimoto et al) issued May 19, 1987, and U.S. Pat. No. 4,625,001 (Tsubakimoto et al) issued Nov. 25, 1986, all of which are incorporated by reference.

Preferred hydrogel-forming absorbent polymers have relatively high gel permeability when swollen with fluid. Gel permeability (also referred to as "flow conductivity") is defined herein in terms of the Saline Flow Conductivity (SFC) value of the hydrogel-forming absorbent polymer. SFC measures the ability of a formed hydrogel region or layer to transport or distribute fluids under usage pressures.

Hydrogel-forming absorbent polymers having relatively high gel permeability are described in copending U.S. application Ser. No. 219,574 (Goldman et al) filed Mar. 29, 1994, now U.S. Pat. No. 5,599,335 issued Feb. 4, 1997, which is incorporated herein by reference. As described in U.S. application Ser. No. 219,574, it is believed that when a hydrogel-forming absorbent polymer is present at high concentrations in an absorbent member and then swells to form a hydrogel under usage pressures, the boundaries of the hydrogel come into contact, and interstitial voids in this high-concentration region become generally bounded by hydrogel. When this occurs, a gel-continuous fluid transportation layer or region is formed. It is believed the gel permeability (flow conductivity) properties of this layer are generally reflective of the hydrogel-forming absorbent polymer alone.

As determined by the methods provided in copending U.S. application Ser. No. 219,574, the SFC value of the hydrogel-forming absorbent polymers preferred for use in the present invention is at least about $30\times10^{-7}$ cm³ sec/g, more preferably at least about $50\times10^{-7}$ cm³ sec/g, and most preferably at least about $100\times10^{-7}$ cm³ sec/g. Typically, these SFC values are in the range of from about $30\times10^{-7}$ cm³ sec/g to about $1000\times10^{-7}$ cm³ sec/g, more typically from about $50\times10^{-7}$ cm³ sec/g to about $500\times10^{-7}$ cm³ sec/g, and most typically from $100\times10^{-7}$ cm³ sec/g to about $350\times10^{-7}$ cm³ sec/g.

Another important characteristic of these high gel permeability hydrogel-forming absorbent polymers is their demand absorbency capacity under a high confining pressure. This demand-absorbency capacity is defined in terms of the polymer's Performance Under Pressure (PUP) capacity. PUP capacity measures the ability of a high basis weight layer of the hydrogel-forming absorbent polymer to absorb fluids under usage pressures. When a hydrogel-forming absorbent polymer is incorporated into an absorbent structure at high concentrations, the polymer needs to be capable of absorbing large quantities of fluids in a reasonable time period under usage pressures. Otherwise, the absorbent structure will be less effective at absorbing fluid. When this occurs, it is believed that the absorbent structure is left with insufficient temporary holding capacity to contain subsequent gushes of body fluid and can leak prematurely. Also, to be able to deliver a high storage capacity from an absorbent structure of minimal weight and thickness, the hydrogel-forming absorbent polymer needs to have a relatively high PUP capacity. A relatively high PUP capacity hydrogel-forming polymer is also needed to provide economical absorbent structures.

Usage pressures exerted on the hydrogel-forming absorbent polymer include both mechanical pressures (e.g., exerted by the weight and motions of the user, taping forces, etc.) and capillary pressures (e.g., resulting from the acquisition component(s) in the absorbent core that temporarily hold fluid before it is absorbed by the hydrogel-forming absorbent polymer.) It is believed that a total pressure of about 0.7 psi (5 kPa) is reflective of the sum of these pressures on the hydrogel-forming absorbent polymer as it absorbs body fluids under usage conditions.

The PUP capacity of preferred hydrogel-forming absorbent polymers used in the present invention is generally at least about 23 g/g, preferably at least about 25 g/g, and most preferably at least about 29 g/g. Typically, these PUP capacity values are in the range of from about 23 to about 35 g/g, more typically from about 25 to about 33 g/g, and most typically from about 29 to about 33 g/g.

The following are some specific examples of high gel permeability hydrogel-forming absorbent polymers suitable for use in the present invention:

EXAMPLE 1

Surface Treatment of Nalco 1180 with Ethylene Carbonate

A non-surface-crosslinked particulate partially neutralized sodium polyacrylate hydrogel-forming polymer, obtained from Nalco Chemical Co., Naperville, Ill. (Nalco 1180; lot no. NCGLG3C920E), is used and has the properties listed under Sample 1-1 in Table 1 below. A 20.0 gram aliquot of this hydrogel-forming absorbent polymer is divided equally into two pre-weighed 150×15 mm disposable polystyrene petri dishes. The polymer in each of the petri dishes is spread out over the bottom, so that the particles are generally not piled on top of each other. A PreVal Spray Gun (Precision Valve Corp; Yonkers, N.Y.) is used to deposit 2.0 g of a 50 weight percent aqueous solution of ethylene carbonate (1,3-dioxolan-2-one; Aldrich cat. no. E2,625-8) on the particles. This corresponds to a 10% weight add-on to the starting polymer. Approximately one-half of the total application is sprayed over exposed surfaces of the particles in the two petri dishes. This causes the particles to generally adhere in a sheet-like structure. The petri dishes are covered, inverted, and tapped so that, for each petri dish, the sheet-like structure is transferred to the inverted cover of the petri dish and the bottom surfaces of the particles are exposed. Particles adhering to the bottom of the petri dish are scrapped off and transferred to the inverted cover. The second half of the application is then applied. The inverted cover of the petri dish is then covered by the inverted bottom of the petri dish. The entire system (petri dish bottom, petri dish cover, hydrogel-forming polymer, and applied ethylene carbonate solution) is weighed. The total weight of ethylene carbonate solution deposited in both petri dishes is determined gravimetrically, by difference from the combined weight prior to spraying.

The treated hydrogel-forming absorbent polymer is transferred to a Number 20 U.S.A Standard Testing Sieve (850 micron opening). The sheet-like structure is gently disrupted with gentle pressure using a spatula and plastic scoop so that the bulk of the polymer passes through the screen and is collected in a pan. Some physical losses occur during this process. The particulate polymer is transferred to a tarred glass beaker and covered with a watch glass. The sample is then placed into a pre-heated Despatch LFD Forced Air Oven that is preset at a temperature of 195° C. It is removed after one hour, placed in a desiccating box over Drierite, and reweighed after cooling to ambient temperature. The percent weight loss as a result of beating is 12.2%.

The resultant surface-treated polymer particles tend to adhere to each other. The particulate mass is gently disrupted with a spatula and transferred back to the No. 20 sieve. The bulk of the particles passes through the sieve upon gentle agitation and pressure and are collected in the pan. Some slight additional physical losses occur during this process. The surface-treated polymer particles are then transferred to a tarred bottle for weighing and storage. A product weight of 17.4 grams is obtained.

The properties of these surface-treated polymer particles (Sample 1-2) are shown in Table 1 below:

TABLE 1

| Sample Code | Mass Median (microns) | Gel Volume (g/g) | Extractables (weight %) | PUP Capacity (g/g) | SFC Value[1] ($10^{-7} \times$ cm³sec/gm) |
|---|---|---|---|---|---|
| 1-1[2] | 400 | 42.2 | 9 | 8.6 | 0.073[3] |
| 1-2 | 450 | 35.6 | 7 | 29.3 | 115 |

[1]Average of three determinations
[2]Base polymer for preparation of sample 1-2 (prior to surface crosslinking)
[3]The absorption time for Jayco SynUrine is extended to 16 hours for this sample

EXAMPLE 2
Surface Treatment of Nalco 1180 with Ethylene Carbonate at Different Levels The surface-treatment procedure described in Example 1 is repeated on two additional 20.0 gram aliquots of the Nalco 1180 particulate hydrogel-forming absorbent polymer, but varying the percent add-on of 50% aqueous ethylene carbonate solution and reducing the oven temperature to 185° C. Again, each of the 20.0 gm aliquots is divided evenly into two polystyrene petri dishes for the deposition of the ethylene carbonate solution. The surface treated samples are again heated for a time period of one hour. The properties these surface-treated polymer particles are shown in Table 2 below:

TABLE 2

| Sample Code | Ethylene Carbonate Solution (wt. %) | Weight Loss at 185° C. (%) | Mass Median (microns) | Gel Volume (g/g) | Extractables (weight %) | PUP Capacity (g/g) | SFC Value[1] ($10^{-7} \times$ cm³sec/gm) |
|---|---|---|---|---|---|---|---|
| 2-1 | 10.5 | 12.0 | 470 | 38.2 | 7 | 30.6 | 44 |
| 2-2 | 20.0 | 17.1 | 460 | 36.0 | 7 | 30.0 | 69 |

[1]Average of three determinations

EXAMPLE 3
Hydrogel-Forming Absorbent Polymers from Commercial Sources

The properties of certain particulate partially-neutralized sodium polyacrylate hydrogel-forming absorbent polymers obtained from commercial sources having high gel permeability properties are shown in Tables 3-1 and Table 3-2:

TABLE 3-1

| Sample Code | Manufacturer | Sample Designation | Lot # |
|---|---|---|---|
| 3-1 | Stockhausen[1] | W52521 | |
| 3-2 | " | W52503 | |
| 3-3 | " | W52523 | |
| 3-4 | Nalco Chemical Co.[2] | XP-30 | 3707-90A |
| 3-5 | " | XP-30 | 3815-64 |
| 3-6 | Chemdal Corp.[3] | ASAP-1001 | 3373 |
| 3-7 | " | " | 00842 |

[1]Stockhausen, Chemische Fabrik Stockhausen GmbH of Krefeld, Germany
[2]Nalco Chemical Company of Naperville, Illinois
[3]Chemdal Corporation of Palatine, Illinois

TABLE 3-2

| Sample Code | Mass Median (microns) | Gel Volume (g/g) | Extractables (weight %) | PUP Capacity (g/g) | SFC Value[1] ($10^{-7} \times$ cm³sec/gm) |
|---|---|---|---|---|---|
| 3-1 | 430 | 29.1 | 5 | 25.9 | 166 |
| 3-2 | 500 | 30.3 | 7 | 25.2 | 130 |
| 3-3 | 360 | 35.7 | 5 | 29.9 | 61 |
| 3-4 | 360 | 34.7 | 4 | 29.9 | 49 |
| 3-5 | 390 | 35.2 | 4 | 30.9 | 57 |
| 3-6 | 500 | 35.4 | 15 | 23.6 | 93 |
| 3-7 | 440 | 37.2 | 13 | 23.4 | 70 |

[1]Average of three determinations

EXAMPLE 4
Selected Size Fractions of Hydrogel-Forming Absorbent Polymers

Selected size fractions of particulate partially neutralized sodium polyacrylate hydrogel-forming absorbent polymers having high gel permeability are obtained by size fractionation of the bulk polymers through U.S.A. Standard Testing Sieves. The properties of these fractionated samples are shown in Table 4 below:

TABLE 4

| Sample Code | Sample Source | Size Fraction (microns) | Gel Volume (g/g) | Extractables (weight %) | PUP Capacity (g/g) | SFC Value[1] ($10^{-7} \times cm^3 sec/g$) |
|---|---|---|---|---|---|---|
| 4-1 | * | 500–710 | 44.4 | 10 | 30.5 | 35 |
| 4-2 | 3-2 | 500–710 | 29.6 | 7[2] | 25.2 | 206 |
| 4-3 | 3-1 | 500–710 | 28.2 | 4 | 25.7 | 355 |
| 4-4 | " | 355–500 | 29.2 | 6 | 26.4 | 252 |
| 4-5 | " | 250–355 | 30.3 | 6 | 26.9 | 166 |
| 4-6 | " | 180–250 | 30.0 | 6 | 27.2 | 90 |

[1] Average of three determinations
[2] Estimated from value for source sample (#3-2).
*Unfractionated sample source is L-761f lot no. 2T12, obtained from Nippon Shokubai of Osaka, Japan. The source polymer has the following properties: mass median size, 390 microns; gel volume, 41.4 g/g; extractables, 10 wt %; PUP capacity, 29.4 g/g; SFC value, 18 $\times 10^{-7}$ $cm^3 sec/gm$.

D. Zones Substantially Devoid of Hydrogel-Forming Absorbent Polymer

The continuous region at least partially surrounds the multiple, spaced apart zones between the first and second layers. As used herein, a "zone" means an area that is considerably greater than the interstitial voids that typically exist between adjacent, dry particles of hydrogel-forming absorbent polymer when the particles are substantially uniformly distributed between layers. These zones are substantially devoid of hydrogel-forming absorbent polymer. For purposes herein, "substantially devoid" of hydrogel-forming absorbent polymer means less than about 6.0%, preferably less than about 2.0%, more preferably less than about 1%, most preferably essentially zero weight percent hydrogel-forming absorbent polymer. As used herein, "essentially zero" percent hydrogel-forming absorbent polymer means low amounts (less than about 0.5%) of hydrogel-forming absorbent polymer present in the zones incidental to the contact or close proximity of the continuous region of hydrogel-forming absorbent polymer.

The zones have at least one dimension of at least about 2 mm. Preferably, the zones have at least one dimension that is from about 3 mm to about 100 mm, more preferably from about 4 mm to about 50 mm, and most preferably from about 5 mm to about 30 mm. In addition to size, the zones can vary in shape and number, and can be present in a regular or irregular pattern within the continuous region of hydrogel-forming absorbent polymer. In particular, the invention is not limited to size, shape, number and pattern for the zones described hereafter in connection with the example drawing.

The presence of multiple zones substantially devoid of hydrogel-forming absorbent polymer provide additional room into which the hydrogel-forming absorbent polymer can expand as it swells without excessive constraint. These zones also provide a medium for distributing the fluid to the various portions of the hydrogel-forming absorbent polymer in the continuous region. These zones can also provide desirable locations for bonding the two layers together, as described hereafter. When permanent bonding occurs around the periphery of a zone (further described below), such zones will provide permanent open voids in the structure, even when the absorbent polymer is in the wetted, swollen state. This may enhance the ability of the fluid to be distributed to other components of an article containing the present absorbent structures.

E. Bonding of Layers

To provide desired dry and wet integrity for the absorbent structures of the present invention, the first and second layers are bonded together. As used herein "bonded" does not refer to the hydrogen bonding that may exist between fibers or fibers and particles within the structure which typically releases when the structure is wetted, but rather to bonding obtained by other means. For example, these layers can be bonded together in a variety of ways, using glue spray, particulate hot melt glues, or heat.

The preferred method according to the present invention is to bond the first and second layers together at sites within a plurality of the zones that are substantially devoid of hydrogel-forming absorbent polymer. Adhesive, heat, or ultrasonic bonding is suitable, although the particular type of bonding used may be limited to some extent by the types of materials used for the first and second layers. This is particularly true if heat or ultrasonic bonding is employed, inasmuch as the materials comprising the layers should be capable of being thermally fused together. The size and spacing of the bonding sites should be chosen to ensure the integrity of absorbent structure will be maintained when dry and when wetted in use, and can vary depending on the particular application.

Bonding of the first and second layers is not limited to spot bonding. For example, the layers can be bonded around the periphery of a plurality of the zones, to provide permanent, open voids.

F. Absorbent Structure Embodiment

FIG. 1 shows an absorbent structure embodying the present invention. The absorbent structure 1 comprises a first layer 2, and a second layer 3 juxtaposed in facing relation with layer 2. Particles of hydrogel-forming absorbent polymer 4 are substantially uniformly distributed in a continuous region between layers 2 and 3. The continuous region 5 surrounds multiple, spaced apart zones 6 of substantial area between layers, which zones are substantially devoid of hydrogel-forming absorbent polymer.

In the embodiment of FIG. 1, absorbent structure 1 is about 10 cm in width and about 30 cm in length. Zones 6 are spaced about 35 mm apart, center to center, across the width and length of the structure. Each zone 6 occupies a generally circular area, as viewed from a vantage point perpendicular to the plane of the layers, of about 200 $mm^2$.

Referring again to FIG. 1, layers 2 and 3 are bonded together with thermal bonds 7. Thermal bonds 7 are centered in some of the zones 6, and each bond occupies a generally circular area, as viewed from a vantage point perpendicular to the plane of the structure, of about 7 $mm^2$. Layers 2 and 3 are also bonded together along thermal bond line 8 which lies adjacent the outer perimeter of absorbent structure 1.

A variety of methods can be used to make the absorbent structures shown in FIG. 1. One such method comprises superimposing a first layer on a porous screen having multiple spaced apart, nonporous, protruding areas corresponding to the areas desired for the zones that are to be substantially devoid of hydrogel-forming polymer. A vacuum is introduced under the porous screen opposite the superimposed layer, and particles of hydrogel-forming absorbent polymer are substantially uniformly distributed across the length and width of the superimposed layer. The particles are then caused by the combination of vacuum and protruding areas to migrate to the areas between the protruding areas to form a substantially uniform distribution in a continuous region on the layer which surrounds multiple zones which are substantially devoid of hydrogel-forming polymer. Thereafter, the particles are misted with a water spray, and a second layer is juxtaposed in facing relation onto the first layer to cover the hydrogel-forming polymer. Finally, the two layers are bonded together, for example via thermal bonding, at locations within a plurality of the zones that are substantially devoid of hydrogel-forming polymer and, if desired, along the perimeter of the absorbent structure.

G. Absorbent Articles

Because of the unique absorbent properties of the absorbent structures of the present invention, they are especially suitable for use as absorbent cores in absorbent articles, especially disposable absorbent articles. As used herein, the term "absorbent article" refers to articles that absorb and contain body fluids, and more specifically refers to articles that are placed against or in proximity to the body of the wearer to absorb and contain the various fluids discharged from the body. Additionally, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted). A preferred embodiment of a disposable absorbent article according to the present invention is a diaper. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, catamenial pads, sanitary napkins, facial tissues, paper towels, and the like. It should be further understood that the absorbent structures of the present invention can be sized and constructed as appropriate for such diapers and such other absorbent articles.

These absorbent articles typically comprise a fluid impervious backsheet, a fluid pervious topsheet joined to, or otherwise associated with the backsheet, and an absorbent structure or core according to the present invention positioned between the backsheet and the topsheet. The topsheet is positioned adjacent the body surface of the absorbent core. The topsheet is preferably joined to the backsheet by attachment means such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In preferred absorbent articles, the topsheet and the backsheet are joined directly to each other at the periphery thereof. The topsheet and backsheet can also be indirectly joined together by directly joining them to the absorbent core by the attachment means.

The backsheet is typically impervious to body fluids and is preferably manufactured from a thin plastic film, although other flexible fluid impervious materials may also be used. As used herein, the term "flexible" refers to materials that are compliant and will readily conform to the general shape and contours of the human body. The backsheet prevents body fluids absorbed and contained in the absorbent core from wetting articles that contact the such as pants, pajamas, undergarments, and the like. The backsheet can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet can permit vapors to escape from the absorbent core (i.e., breathable) while still preventing body fluids from passing through the backsheet.

The topsheet is compliant, soft feeling, and non-irritating to the wearer's skin. Further, the topsheet is fluid pervious permitting body fluids to readily penetrate through its thickness. A suitable topsheet can be manufactured from a wide range of materials such as woven and nonwoven materials; polymeric materials such as apertured formed thermoplastic films, apertured plastic films, and hydroformed thermoplastic films; porous foams; reticulated foams, reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Preferred topsheets for use in absorbent articles of the present invention are selected from high loft nonwoven topsheets and aperture formed film topsheets. Apertured formed films are especially preferred for the topsheet because they are pervious to body fluids and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson) issued Dec. 30, 1975, U.S. Pat. No. 4,324,246 (Mullane, et al.) issued Apr. 13, 1982, U.S. Pat. No. 4,342,314 (Radel. et al.) issued Aug. 3, 1982, U.S. Pat. No. 4,463,045 (Ahr et al.) issued Jul. 31, 1984, and U.S. Pat. No. 5,006,394 (Baird) issued Apr. 9, 1991. Each of these patents are incorporated herein by reference. Particularly preferred microapertured formed film topsheets are disclosed in U.S. Pat. No. 4,609, 518 (Curro et al) issued Sep. 2, 1986 and U.S. Pat. No. 4,629,643 (Curro et al) issued Dec. 16, 1986, which are incorporated by reference. The preferred topsheet for use in catamenial products of the present invention is the formed film described in one or more of the above patents and marketed on sanitary napkins by The Procter & Gamble Company of Cincinnati, Ohio as "DRI-WEAVE®."

The body surface of the formed film topsheet can be hydrophilic so as to help body fluids to transfer through the topsheet faster than if the body surface was not hydrophilic so as to diminish the likelihood that fluid will flow off the topsheet rather than flowing into and being absorbed by the absorbent structure. In a preferred embodiment, surfactant is incorporated into the polymeric materials of the formed film topsheet such as is described in U.S. patent application Ser.

No. 07/794,745, "Absorbent Article Having A Nonwoven and Apertured Film Coversheet" filed on Nov. 19, 1991 by Aziz, et al., which is incorporated by reference. Alternatively, the body surface of the topsheet can be made hydrophilic by treating it with a surfactant such as is described in the above referenced U.S. Pat. No. 4,950,254, incorporated herein by reference.

We claim:

1. An absorbent structure comprising:
   (a) a first layer;
   (b) a second layer juxtaposed in facing relation with said first layer;
   (c) a continuous region between said first and second layers comprising substantially discrete particles of hydrogel-forming absorbent polymer substantially uniformly distributed throughout said region;
   (d) said continuous region at least partially surrounding multiple, spaced apart zones between said layers, said zones being substantially free of said hydrogel-forming absorbent polymer;
   (e) said said first and second layers being bonded together such that said hydrogel-forming absorbent polymer is substantially immobilized when in a dry state;
   (f) wherein at least one of said layers is fluid pervious; and
   (g) wherein said first and second layers are bonded together at a site within at least one of said zones.

2. The structure of claim 1 wherein one of said layers is fluid impervious.

3. The structure of claim 1 wherein at least one of said layers is extensible so as to have a percent stretch of at least about 5%.

4. The structure of claim 1 wherein each fluid pervious layer comprises fibers.

5. The structure of claim 4 wherein each fluid pervious layer further comprises thermoplastic material.

6. The structure of claim 1 wherein said continuous region has a hydrogel-forming absorbent polymer concentration of at least about 0.001 g/cm$^2$.

7. The structure of claim 1 wherein said continuous region has a hydrogel-forming absorbent polymer concentration of at least about 0.010 g/cm$^2$.

8. The structure of claim 1 wherein said zones have at least one dimension of at least about 2 mm.

9. The structure of claim 1 wherein said zones have at least one dimension of from about 4 mm to about 50 mm.

10. The structure of claim 1 wherein said zones comprise less than about 2% by weight of hydrogel-forming absorbent polymer.

11. The structure of claim 1 wherein said zones comprise less than about 1% by weight of hydrogel-forming absorbent polymer.

12. The structure of claim 1 wherein said first and second layers are bonded together at sites within a plurality of said zones.

13. The structure of claim 1 wherein said first and second layers are bonded together around the periphery of a plurality of said zones.

14. An absorbent structure comprising:
   (a) a first layer;
   (b) a second layer juxtaposed in facing relation with said first layer;
   (c) a continuous region between said first and second layers comprising substantially discrete particles of high gel permeability hydrogel-forming absorbent polymer substantially uniformly distributed throughout said region;
   (d) said continuous region at least partially surrounding multiple, spaced apart zones between said layers, said zones being substantially free of said hydrogel-forming absorbent polymer;
   (e) said first and second layers being bonded together at a site within at least one of said zones and such that said hydrogel-forming absorbent polymer is substantially immobilized when in a dry state; and
   (f) wherein at least one of said layers is fluid pervious.

15. The structure of claim 14 wherein said hydrogel-forming absorbent polymer forms a gel-continuous fluid transportation region.

16. The structure of claim 14 wherein said hydrogel-forming absorbent polymer has a saline flow conductivity value of at least about $50 \times 10^{-7}$ cm$^3$ sec/g.

17. The structure of claim 14 wherein said hydrogel-forming absorbent polymer has a saline flow conductivity value of at least about $100 \times 10^{-7}$ cm$^3$ sec/g.

18. The structure of claim 14 wherein said high gel permeability hydrogel-forming absorbent polymer has a performance under pressure capacity of at least about 23 g/g.

19. A disposable diaper comprising:
   (a) a fluid pervious topsheet;
   (b) a fluid impervious backsheet associated with said topsheet; and
   (c) an absorbent structure positioned between said topsheet and backsheet, said structure comprising:
      (1) a first layer;
      (2) a second layer juxtaposed in facing relation with said first layer;
      (3) a continuous region between said first and second layers comprising substantially discrete particles of hydrogel-forming absorbent polymer substantially uniformly distributed throughout said region;
      (4) said continuous region at least partially surrounding multiple, spaced apart zones between said layers, said zones being substantially free of said hydrogel-forming absorbent polymer;
      (5) said first and second layers being bonded together at a site within at least one of said zones and such that said hydrogel-forming absorbent polymer is substantially immobilized when in a dry state; and
      (6) wherein at least one of said layers is fluid pervious.

20. The disposable diaper of claim 19 wherein said hydrogel-forming absorbent polymer has high gel permeability.

* * * * *

UNITED STATES PATENT AND TRADEMARK OFFICE
CERTIFICATE OF CORRECTION

PATENT NO. : 5,941,862
DATED : August 24, 1999
INVENTOR(S) : Haynes et al.

It is certified that error appears in the above-identified patent and that said Letters Patent is hereby corrected as shown below:

Column 17, line 22, "said said" should be --said--.

Signed and Sealed this

Eighteenth Day of July, 2000

Attest:

Q. TODD DICKINSON

*Attesting Officer*       *Director of Patents and Trademarks*